(12) United States Patent
Bircoll

(10) Patent No.: US 7,214,235 B2
(45) Date of Patent: May 8, 2007

(54) METHOD OF SKIN LESION EXCISION USING BALLOON DISSECTION

(76) Inventor: Melvin Bircoll, 2700 Casiano Rd., Los Angeles, CA (US) 90077

( * ) Notice: Subject to any disclaimer, the term of this patent is extended or adjusted under 35 U.S.C. 154(b) by 759 days.

(21) Appl. No.: 10/374,666

(22) Filed: Feb. 24, 2003

(65) Prior Publication Data

US 2003/0216751 A1  Nov. 20, 2003

Related U.S. Application Data

(63) Continuation of application No. 09/683,443, filed on Dec. 31, 2001, now abandoned.

(51) Int. Cl.
*A61B 17/00* (2006.01)

(52) U.S. Cl. ........... 606/190; 128/898

(58) Field of Classification Search ........ 606/190, 606/192, 131; 604/96, 97, 98–104; 600/207; 128/898

See application file for complete search history.

(56) References Cited

U.S. PATENT DOCUMENTS

| 5,328,469 | A | * | 7/1994 | Coletti | 604/103.09 |
| 5,452,732 | A | * | 9/1995 | Bircoll | 128/898 |
| 5,746,762 | A | * | 5/1998 | Bass | 606/192 |
| 5,979,452 | A | * | 11/1999 | Fogarty et al. | 128/898 |

* cited by examiner

*Primary Examiner*—Michael J. Hayes
*Assistant Examiner*—Victor X. Nguyen
(74) *Attorney, Agent, or Firm*—Mark Ogram

(57) ABSTRACT

A method of performing skin lesion excision using balloon dissectors. The method's principle benefits are: (1) a reduction in the amount of time it takes the surgeon to create a surgical field with properly undermined and hemostatically controlled skin flaps, (2) a reduction in the amount of tension on the skin closure, and (3) an increase in the likelihood of optimal scar formation.

17 Claims, 2 Drawing Sheets

METHOD OF SKIN LESION EXCISION USING BALLOON DISSECTION

This is a continuation of U.S. patent application Ser. No. 09/683,443, filed on Dec. 31, 2001, now abandoned and entitled, "Method of Skin Lesion Excision Using Balloon Dissection".

BACKGROUND OF INVENTION

This invention relates to surgical techniques in general and more specifically to the surgical techniques involved in removing skin lesions, whether for biopsy (i.e., to determine the nature of the lesion), for cosmetic reasons or for tumor removal. The general and accepted current method of skin lesion excision is to mark a pattern of excision in accordance with the type of flap repair contemplated (e.g., an ellipse for linear advancement flap repair, a V for a V-Y flap repair, etc.). The flap pattern is excised and the lesion is removed in accordance with the pattern chosen. Full-thickness skin with margins surrounding the lesion is removed. At this point, electrocautery is used to control bleeding. The edges of the excised margins are elevated to allow for some tension on these edges and then a sharp instrument (e.g., a scalpel blade or a scissors) is used to create flaps of skin on all margins of the excised wound. The margins are then undermined for some distance to allow the flaps to be advanced into a position of closure such that they do not have any tension, or have minimal tension placed upon them at the time of closure. Following this step, another session of electrocautery is used to control bleeding under the flaps. The wound margins are then approximated (i.e., closed) using suture and/or skin adhesive techniques.

Dissecting surgical tools have been used almost since the dawn of history. These tools are generally divided into tools for blunt dissection and tools for sharp/cutting dissection. As the name implies, sharp/cutting dissection involves the actual cutting of tissue; blunt dissection, on the other hand, separates along natural lines within the body by breaking the connective tissue.

The breaking of connective tissue is generally easily accomplished using a variety of tools well known in the surgical fields. Examples of tools which utilize a traditional blunt dissection are described in: "Bulbous-Lysin undermines" by Weber et al. and appearing in *Dermatological Surgery and Oncology,* 15:12, December 1989, page 1252; U.S. Pat. No. 4,815,465, entitled "Dissector Device", issued to Alvarado on Mar. 28, 1989; U.S. Pat. No. 5,188,630, entitled "Christoudias: Endopongestick Probe", issued to Christoudias on Feb. 23, 1993; U.S. Pat. No. 5,022,414, entitled "Tissue Separator Method", issued to Muller on Jun. 11, 1991. In all of these devices, a substantially rigid member is pressed against the connective tissues to break them.

In another field of medicine, a "dissection-type" of operation is done in which balloons are used to break plaque build-up in the arterial walls. This operation, named angioplasty, uses a balloon that is inflated in the artery, thereby pressing the plaque against the artery's wall so that the bonding is broken therebetween. Examples of these devices are shown by U.S. Pat. No. 5,250,060, entitled "Angioplasty Appartus", issued to Carbo et al. on Oct. 5, 1993; U.S. Pat. No., 4,685,458, entitled "Angioplasty Catheter and Method of Use Thereof", issued to Leckrone on Aug. 1, 1987; U.S. Pat. No. 4,747,405, entitled "Angioplasty Catheter", issued to Leckrone on May 31, 1988; and U.S. Pat. No. 5,219,355, entitled "Balloon Device for Implanting an Aortic Intraluminal Prosthesis for Repairing Aneurysms", issued to Parodi et al. on Jun. 15, 1993. None of these devices, though, is a true dissector in that none breaks the connective tissue. Instead, these devices break only the plaque bonding's grip.

Some attempts have been made to use balloons in areas other than in the angioplasty field. One such example is described in U.S. Pat. No. 5,195,507, entitled "Endoscopic Surgical Instrument for Displacing Tissue or Organs", issued to Bilweis on Mar. 23, 1993. As the title implies though, the balloon acts to merely replace or nudge the organ and no actual dissection occurs. Further, for all intents and purposes, the balloon (being made of rubber or an elastic material) is of an indeterminate size and shape, thereby limiting its application to only a few areas.

It is clear that while dissecting remains an integral part of surgery, there had not been any real development in instruments which are either tailored for specific applications, or which accomplish the actual dissecting in a gentle and controlled manner—until the advent of the following patents: U.S. Pat. No. 5,452,732, entitled "Method of Dissecting Along Connective Tissue Lines", issued to Bircoll on Sep. 26, 1995; U.S. Pat. No. 5,549,625, entitled "Balloon Dissector", issued to Bircoll on Aug. 27, 1996; and U.S. Pat. No. 5,725,545, entitled "Balloon Dissector", issued to Bircoll on Mar. 10, 1998 (collectively, the "Bircoll Patents").

DETAILS OF INVENTION

This invention is an improved technique for performing skin lesion excision.

In this technique, a balloon dissector—having a predetermined inflated size and shape—is placed between two naturally occurring layers in the subcutaneous tissue. The balloon is then inflated to its full size to force these layers apart and to create properly undermined, hemostatically controlled flaps. After the inflated balloon dissector has been in place for approximately two minutes, the balloon dissector is removed. The skin lesion is sharply excised and then closed with sutures and/or skin adhesives.

The principle benefits of this new method of performing skin lesion excision include: (1) a reduction in the amount of time it takes the surgeon to create a surgical field with properly undermined and hemostatically controlled skin flaps, (2) a reduction in the amount of tension on the skin closure, and (3) an increase in the likelihood of optimal scar formation.

In more detail, with the advent of the Bircoll Patents, including balloon dissectors, new methods of performing traditional surgical procedures are available. Among these is a new method of performing skin lesion excision. The disclosed invention details this new method of performing skin lesion excision—a method of performing skin lesion excision using balloon dissectors. The method's principle benefits are: (1) a reduction in the amount of time it takes the surgeon to create a surgical field with properly undermined and hemostatically controlled skin flaps, (2) a reduction in the amount of tension on the skin closure, and (3) an increase in the likelihood of optimal scar formation.

The first step in performing the method disclosed in this invention is the same as the first step in the general and accepted current method of skin lesion excision: the surgeon marks a pattern of skin excision in accordance with the type of flap repair contemplated (e.g., an ellipse for linear advancement flap repair, a V for a V-Y flap repair, etc.). Next, the surgeon makes a small incision just large enough to allow for the introduction of a small instrument at one end of the markings. For example, if an elliptical incision is contemplated, the access incision is a small V incision at one end of the ellipse. Through the access incision, a deflated balloon dissector—which may itself be marked with indices for proper orientation and which has a predetermined inflated size and shape—is introduced into the subcutaneous tissue underneath the lesion to be excised. The balloon dissector is then inflated to a proper volume with a sterile fluid (e.g., water or saline). This inflation creates the undermined flaps in the subcutaneous plane. The balloon dissector is left in the inflated state for approximately two minutes to affect a capillary hemostasis, and then removed. The surgical field having been thus prepared, the lesion is then sharply (e.g., with a scalpel) excised. Finally, the surgeon closes the prepared flaps with sutures and/or skin adhesives.

The invention, together with variations on the method, will be more fully explained by the accompanying drawings and the following description thereof.

BRIEF DESCRIPTION OF DRAWINGS

As noted earlier, the invention involves the first step which is the same as the first step in the general and accepted current method of skin lesion excision: the surgeon marks a pattern of skin excision in accordance with the type of flap repair contemplated (e.g., an ellipse for linear advancement flap repair, a V for a V-Y flap repair, etc.). Next, the surgeon makes a small incision just large enough to allow for the introduction of a small instrument at one end of the markings. For example, if an elliptical incision is contemplated, the access incision is a small V incision at one end of the ellipse. Through the access incision, a deflated balloon dissector—which may itself be marked with indices for proper orientation and which has a predetermined inflated size and shape—is introduced into the subcutaneous tissue underneath the lesion to be excised. The balloon dissector is then inflated to a proper volume with a sterile fluid (e.g., water or saline). This inflation creates the undermined flaps in the subcutaneous plane. The balloon dissector is left in the inflated state for approximately two minutes to affect a capillary hemostasis, and then removed. The surgical field having been thus prepared, the lesion is then sharply (e.g., with a scalpel) excised. Finally, the surgeon closes the prepared flaps with sutures and/or skin adhesives.

Figure 1:
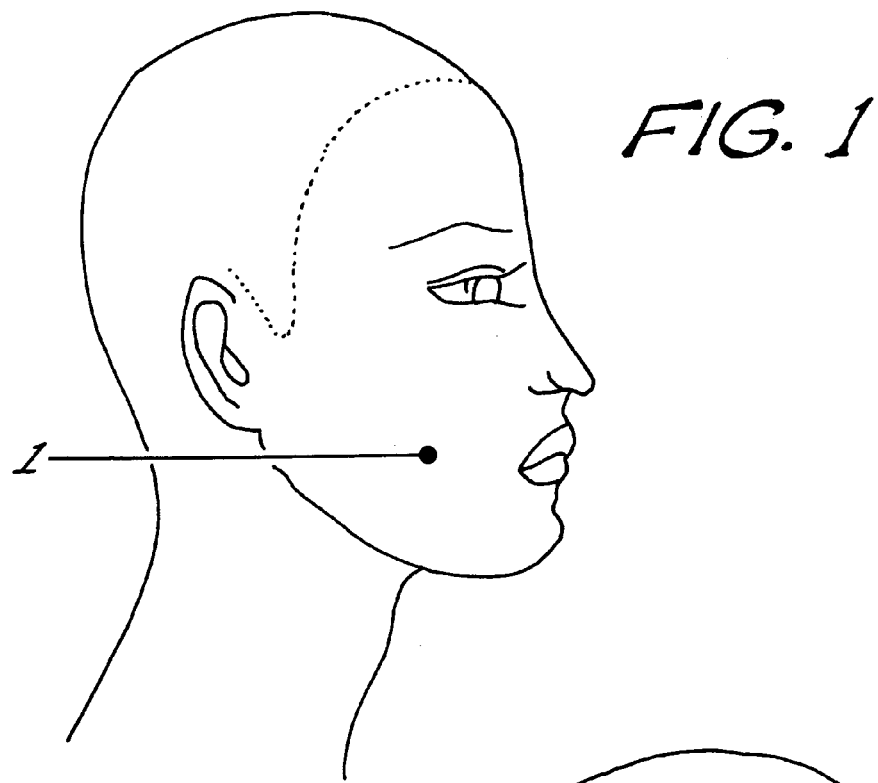
FIG. 1 illustrates a skin lesion 1 on the cheek. The skin lesion 1 will be removed using the invention method (e.g., balloon dissection).
Figure 2:
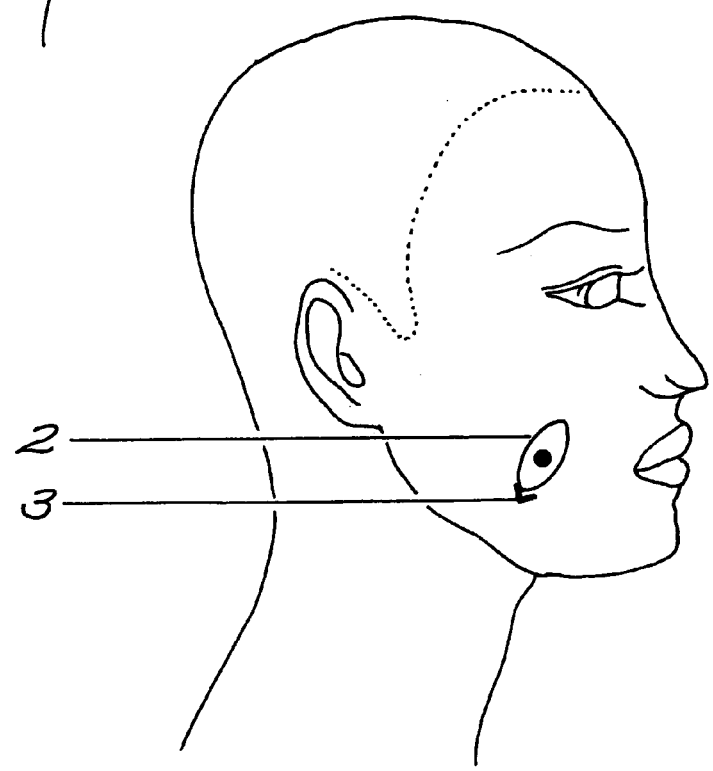
FIG. 2 shows an ellipse 2 marked on the skin. The marked ellipse 2 surrounds the skin lesion with margins of normal skin and is placed into relaxed skin tension lines. A small "V" 3 is incised of the marking of the ellipse 2 which will be the entry portal, into the subcutaneous plane, for placement of a balloon dissector.
Figure 3:
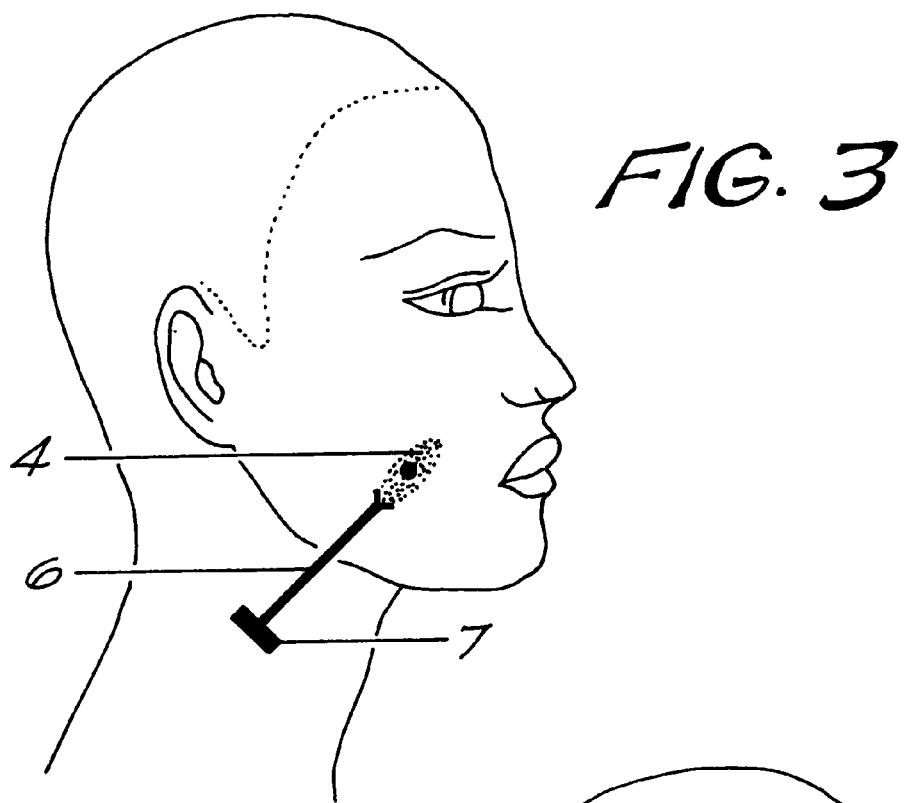
FIG. 3 illustrates a balloon dissector 4 in the deflated state. The expandable balloon 5 of the balloon dissector 4 is placed underneath the skin lesion 1, in the subcutaneous plane. The handle 6, which ends in a connector 7, is shown to be above the skin.
Figure 4:
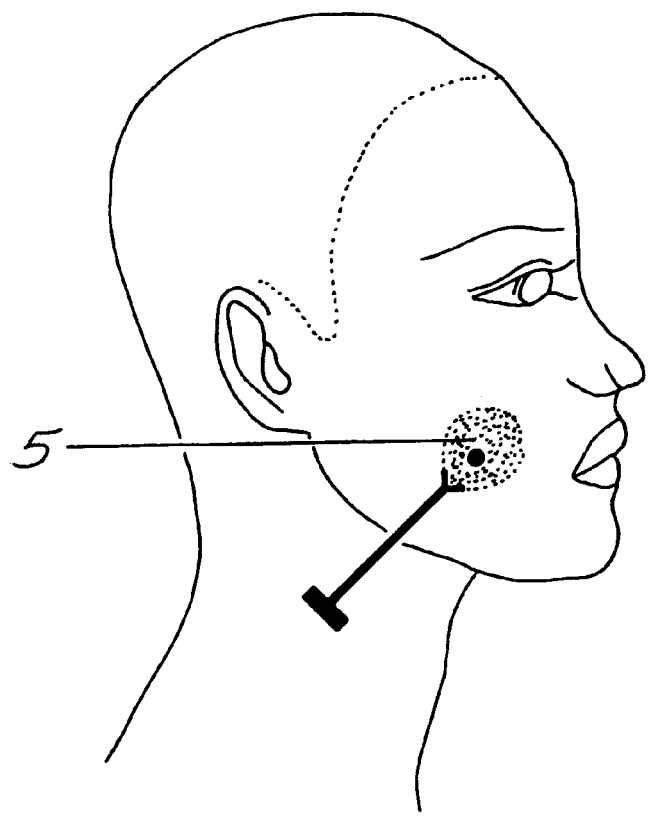
FIG. 4 shows the expandable balloon 5 in the inflated state, in the subcutaneous plane. A syringe (not shown) is attached to the connector 7 through which the expandable balloon 5 is filled. Balloon dissection creates hemostatically secured, undermined flaps in preparation for excision and (in this case advancement flap) closure.

It is clear that the present invention provides for a highly improved method of skin lesion excision.

What is claimed is:

1. A method of skin lesion excision comprising the steps of:
    a) creating a small incision just large enough to allow for the introduction of a small instrument at a surgical site;
    b) inserting a small instrument having a deflated balloon dissector therein through the incision to dissect and position said deflated balloon dissector in subcutaneous tissue beneath a lesion to be excised;
    c) inflating the balloon dissector with a sterile fluid;
    d) maintaining the balloon dissector in an inflated state for a period of time;
    e) deflating said balloon dissector;
    f) removing the deflated balloon dissector from the surgical site; and,
    g) excising the lesion.

2. The method according to claim 1, further including the step of, after the step of position the balloon dissector beneath the lesion, aligning said balloon dissector to a chosen orientation relative to said lesion.

3. The method according to claim 1, wherein said balloon dissector is maintained in an inflated state for a period sufficient to establish capillary hemostasis at the site.

4. The method according to claim 3, wherein said balloon dissector is maintained in an inflated state for at least two minutes.

5. The method according to claim 3, further including the step of, after the step of excising the lesion, closing the prepared flaps.

6. The method according to claim 5, wherein the step of closing the prepared flaps includes the step of suturing the prepared flaps.

7. The method according to claim 5, wherein the step of closing the prepared flaps includes the step of applying skin adhesives to the prepared flaps.

8. A preparatory method for skin lesion excision comprising the steps of:
    a) inserting a deflated balloon dissector through an incision to dissect tissue in order to position said deflated balloon dissector in subcutaneous tissue beneath a lesion to be excised;
    b) inflating the balloon dissector;
    c) maintaining the balloon dissector in an inflated state for a period of time sufficient for capillary hemostasis;
    d) deflating said balloon dissector; and,
    e) removing the deflated balloon dissector.

9. The method according to claim 8, further including the step of aligning said balloon dissector to a chosen orientation relative to the lesion after the step of position the balloon dissector beneath the lesion.

10. The method according to claim 8, wherein said balloon dissector is maintained in an inflated state for at least two minutes.

11. A method of skin lesion excision comprising the steps of:
    a) creating an incision proximate to a lesion;
    b) through said incision, inserting a deflated balloon dissector through the incision to dissect tissue;
    c) positioning said deflated balloon dissector in subcutaneous tissue beneath a lesion to be excised;
    d) inflating the balloon dissector;
    e) maintaining the balloon dissector in an inflated state for a period of time;
    f) deflating said balloon dissector and removing the deflated balloon dissector; and,
    g) excising the lesion.

12. The method according to claim 11, further including the step of aligning said balloon dissector to a chosen orientation after the step of position the balloon dissector beneath the lesion.

13. The method according to claim 11, wherein said balloon dissector is maintained in an inflated state for a period sufficient to establish capillary hemostasis beneath said lesion.

14. The method according to claim 13, wherein said balloon dissector is maintained in an inflated state for at least two minutes.

15. The method according to claim 11, further including the step of closing the prepared flaps.

16. The method according to claim 15, wherein the step of closing the prepared flaps includes the step of suturing the prepared flaps.

17. The method according to claim 15, wherein the step of closing the prepared flaps includes the step of applying skin adhesives to the prepared flaps.

* * * * *